United States Patent
Taylor et al.

(10) Patent No.: US 10,398,852 B2
(45) Date of Patent: Sep. 3, 2019

(54) SMART ADAPTER FOR INFUSION DEVICES

(71) Applicant: Becton, Dickinson and Company, Franklin Lakes, NJ (US)

(72) Inventors: Margaret Taylor, Groton, MA (US); David Feygin, Glen Rock, NJ (US); Elizabeth Nelson, Wellesley, MA (US); Bart Peterson, Farmington, UT (US); Karthik Ranganathan, Singapore (SG); Richard Byrd, Glen Rock, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 23 days.

(21) Appl. No.: 14/776,699

(22) PCT Filed: Mar. 14, 2014

(86) PCT No.: PCT/US2014/027640
§ 371 (c)(1),
(2) Date: Sep. 14, 2015

(87) PCT Pub. No.: WO2014/152704
PCT Pub. Date: Sep. 25, 2014

(65) Prior Publication Data
US 2016/0030683 A1    Feb. 4, 2016

Related U.S. Application Data

(60) Provisional application No. 61/788,506, filed on Mar. 15, 2013.

(51) Int. Cl.
*A61M 5/34*    (2006.01)
*A61M 5/142*    (2006.01)
(Continued)

(52) U.S. Cl.
CPC ........ *A61M 5/345* (2013.01); *A61M 5/14248* (2013.01); *A61M 5/168* (2013.01);
(Continued)

(58) Field of Classification Search
CPC ...... A61M 5/345; A61M 5/4248; A61M 5/32; A61M 5/14244; A61M 5/3155; A61M 37/0015
See application file for complete search history.

(56) References Cited

U.S. PATENT DOCUMENTS 5,593,390 A    1/1997    Castellano et al.
6,374,140 B1 *    4/2002    Rise ................... A61N 1/36064
                                                    600/544
(Continued)

FOREIGN PATENT DOCUMENTS

JP    2004524869 A    8/2004
WO    9215256 A1    9/1992
(Continued)

OTHER PUBLICATIONS

European Search Report dated Nov. 16, 2016 which issued in the counterpart Patent Application No. 14771010.7.
(Continued)

*Primary Examiner* — Jason E Flick
*Assistant Examiner* — Courtney B Fredrickson
(74) *Attorney, Agent, or Firm* — Dickinson Wright PLLC

(57) ABSTRACT

Smart sensors are employed to determine one or more of drug identification, dose, flow rate, concentration, agglomeration, and degradation and/or other characteristics of drug administration that can be detected via sensing technology. A smart sensor(s) can be coupled to or retrofitted onto injection pen injectors and/or drug delivery cartridges and/or infusion sets or cannulae, enabling infusion sets, pen injector systems or drug delivery cartridges to improve tracking of (Continued)

drug self-administration and stop medication errors that occur primarily through self or automated injection (e.g., due to incorrect or incomplete dosing, excessive dose or rate, incorrect drug, or drug degradation).

8 Claims, 15 Drawing Sheets

(51) Int. Cl.
    *A61M 5/32*     (2006.01)
    *A61M 5/168*     (2006.01)
    *A61M 37/00*     (2006.01)
    *A61M 5/315*     (2006.01)

(52) U.S. Cl.
    CPC ........... *A61M 5/32* (2013.01); *A61M 5/14244* (2013.01); *A61M 5/3155* (2013.01); *A61M 37/0015* (2013.01); *A61M 2205/33* (2013.01); *A61M 2205/3317* (2013.01); *A61M 2205/3327* (2013.01); *A61M 2205/3334* (2013.01); *A61M 2205/3368* (2013.01); *A61M 2205/3375* (2013.01); *A61M 2205/3553* (2013.01); *A61M 2205/3561* (2013.01); *A61M 2205/3569* (2013.01); *A61M 2205/50* (2013.01); *A61M 2205/502* (2013.01); *A61M 2205/52* (2013.01)

(56) References Cited

U.S. PATENT DOCUMENTS

| | | | |
|---|---|---|---|
| 7,537,590 B2 | 5/2009 | Santini et al. | |
| 8,206,340 B2 | 6/2012 | Arefieg | |
| 8,385,972 B2 | 2/2013 | Bochenko et al. | |
| 2002/0002326 A1* | 1/2002 | Causey, III | A61B 5/0002 600/300 |
| 2002/0040208 A1* | 4/2002 | Flaherty | A61M 5/14248 604/288.01 |
| 2002/0072733 A1* | 6/2002 | Flaherty | A61M 5/14248 604/890.1 |
| 2004/0171983 A1* | 9/2004 | Sparks | A61M 5/16827 604/65 |
| 2007/0088265 A1* | 4/2007 | Butikofer | A61M 5/1413 604/131 |
| 2010/0069851 A1* | 3/2010 | Vad | A61B 17/3401 604/240 |
| 2011/0046477 A1* | 2/2011 | Hulvershorn | A61B 5/0215 600/424 |
| 2011/0060229 A1* | 3/2011 | Hulvershorn | A61B 5/0215 600/486 |
| 2011/0112474 A1 | 5/2011 | Bochenko et al. | |
| 2011/0144586 A1* | 6/2011 | Michaud | A61M 5/1413 604/151 |
| 2011/0181410 A1 | 7/2011 | Levinson et al. | |
| 2011/0270027 A1* | 11/2011 | Augarten | A61M 5/486 600/37 |
| 2012/0184907 A1* | 7/2012 | Smith | A61M 5/14248 604/152 |
| 2012/0222468 A1* | 9/2012 | Nelson | A61M 5/168 73/61.41 |
| 2012/0226446 A1* | 9/2012 | Nelson | A61M 5/168 702/25 |
| 2014/0276213 A1* | 9/2014 | Bochenko | A61M 39/0208 600/573 |

FOREIGN PATENT DOCUMENTS

| | | |
|---|---|---|
| WO | 2009023247 A1 | 2/2009 |
| WO | 2009114115 A1 | 9/2009 |
| WO | 2012107493 A1 | 8/2012 |
| WO | WO-2012107493 A1 | 8/2012 |

OTHER PUBLICATIONS

English translation of the Japanese Office Action dated Dec. 19, 2017 which issued in the counterpart Patent Application No. 2016-502501.

European Office Action dated Oct. 12, 2018, which issued in the corresponding European Patent Application No. 14 771 010.7.

* cited by examiner

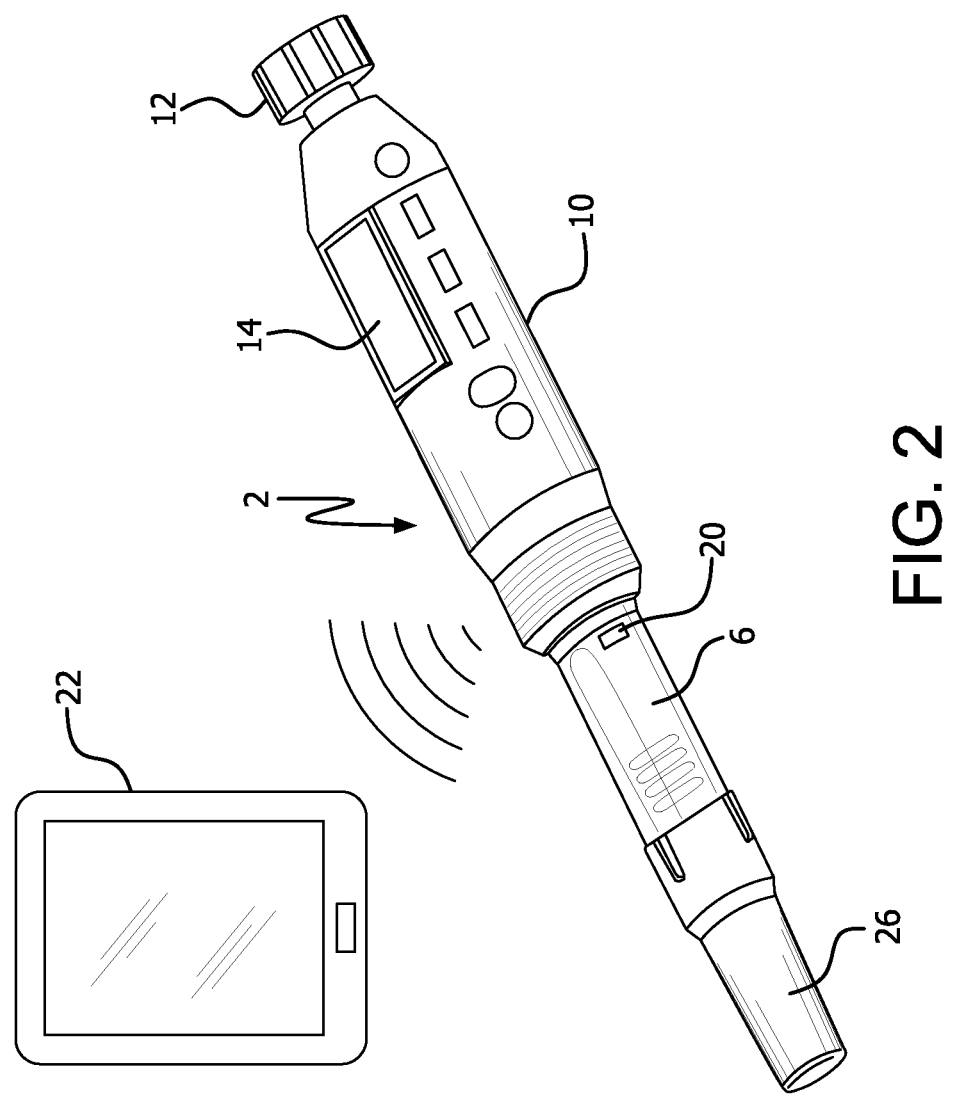

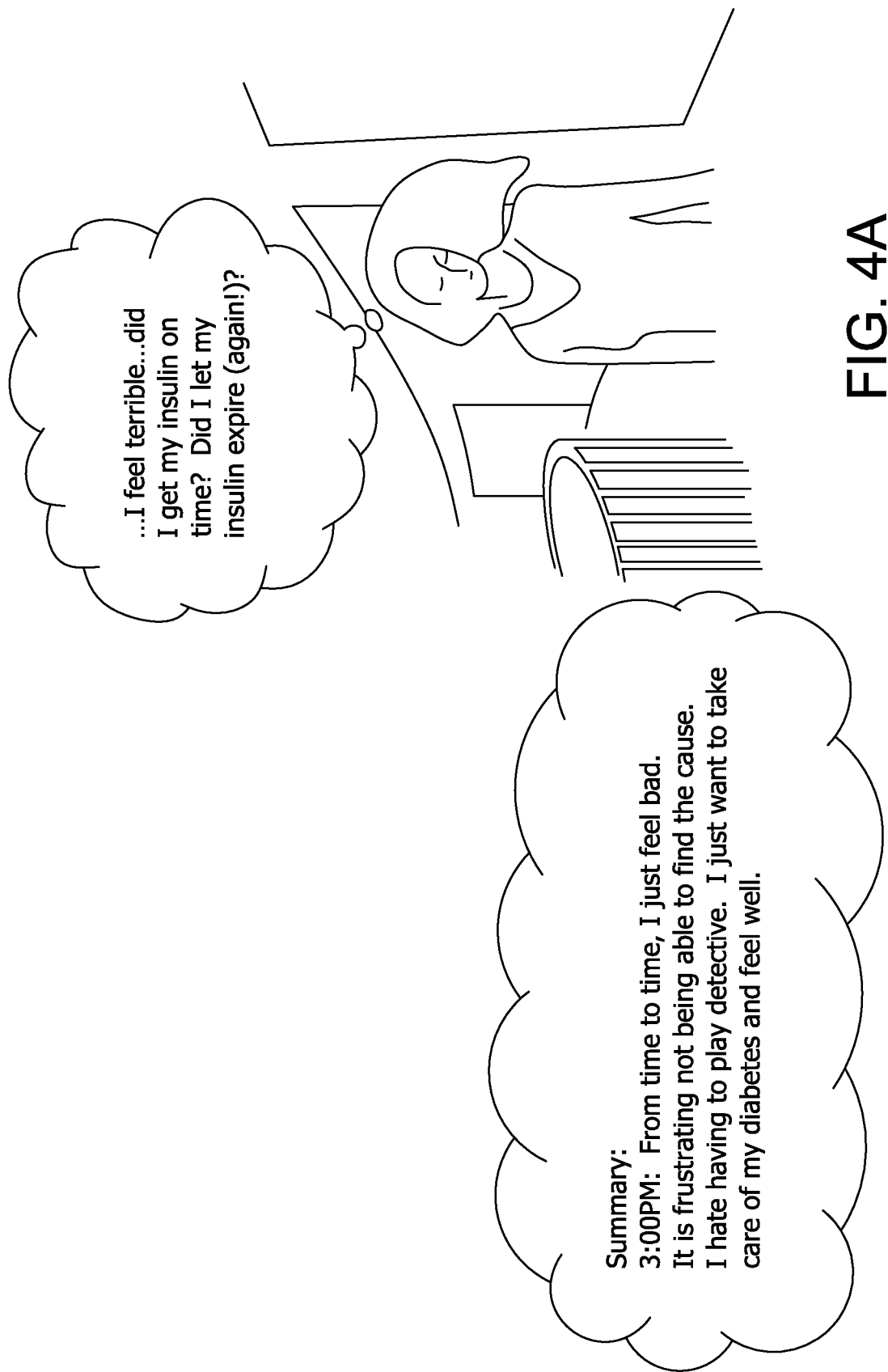

SMART ADAPTER FOR INFUSION DEVICES

FIELD OF THE INVENTION

The present invention relates generally to a smart insulin or medicament delivery device that records, for example, the flow, dose of an insulin or medicament injection and/or other medicament-related parameter or fluid-type medicament delivery parameter, and communicates wirelessly with a portable system and controller.

BACKGROUND OF THE INVENTION

According to the American Diabetes Association, over 23.6 million children and adults within the United States alone (7.8% of the population) have diabetes. About 1 in every 400 to 600 children and adolescents has type 1 diabetes, requiring daily injections of insulin to regulate his/her blood sugar. In adults, type 1 diabetes accounts for 5-10% of all diagnosed cases of diabetes. To manage the injection of insulin on a daily basis, different technologies have emerged to regulate insulin delivery. However, insulin must be regulated on an individual basis. Thus, a dose correct for an adult could be life threatening to a child. Accordingly, regardless of the different technologies in place to regulate insulin, insulin remains one of the top high alert drugs on the Institute for Safe Medication Practices' (ISMP's) list of High-alert Medications.

Insulin is dispensed in units that correspond to an individual's body mass, age, and blood sugar levels. Current injection pens and cartridges accommodate multiple doses so that an individual can dispense the proper amount of insulin and can typically use each pen or cartridge multiple times before it is empty. However, it is becoming increasingly difficult to use these unit doses of insulin to effectively treat diabetic patients in view of growing population trends.

In October 2003, the Centers for Disease Control and Prevention (CDC) reported that the average BMI (i.e., body mass index, which is a weight-for height formula used to measure obesity) has increased among adults from approximately 25 in 1960 to 28 in 2002. Meanwhile, the average weight for men aged 20-74 years rose dramatically from 166.3 pounds in 1960 to 191 pounds in 2002, while the average weight for women the same age also increased dramatically from 140.2 pounds in 1960 to 164.3 pounds in 2002. Insulin manufacturers have responded by creating higher doses of insulin in an effort to accommodate people who require large doses. The American Society of Health-System Pharmacists (ASHP) published an article about the use of concentrated insulin human regular (U-500) and the concerns associated with dispensing at these high doses. This article recommended that the health care professionals be well educated and vigilant about patient safety issues regarding the drug's prescription, dosing, and administration. (Segal, A. R. et al., "Use of Concentrated Insulin Human Regular (U-500) for Patients with Diabetes," American Journal of Health-System Pharmacists, Sep. 15, 2010, 67:1526-1535).

A need therefore exists for a drug delivery device that can help address concerns about high dose insulin and other high alert drugs by ensuring that the drug will be delivered at the correct dose into the patient.

Additionally, insulin and other drugs contained in injection pens are subject to degradation over time. Insulin should be kept refrigerated before use and expires within days once the insulin is in use. Having insulin cartridges that monitor the temperature and/or degradation of the insulin could prevent medication errors that occur due to improper handling, temperature exposure, light exposure or time elapse.

A need therefore also exists for a drug delivery device (e.g., an insulin pump or injection pen needle) that has the capability of accurately verifying a drug before being administered, and/or catching medication errors due to drug expiration, degradation, contamination, and so on.

Also, a need exists for a drug delivery device that has the capability of transferring comprehensive documentation, patient information, and scientific fluid identification, all in one device.

SUMMARY OF THE INVENTION

In accordance with an aspect of the illustrative embodiments of the present invention, a smart sensor can be in-line with respect to a drug delivery system's path of delivery such as, for example, provide all or part of a drug throughway, or be adjacent to the drug throughway such as part of the cannula of an infusion set or needle mechanism of a syringe or pen, or connected to the side of a drug reservoir, cartridge or syringe, or submersed in the drug such as submersed in a cartridge or reservoir of a pump or in a syringe).

The drug delivery system or device with smart sensor(s) described herein in accordance with illustrative embodiments allows for accurate and confirmed delivery of a desired dose of drug, and therefore increases efficacy and safety of the drug's usage, which is helpful to patients prescribed High alert Medications such as insulin and particularly helpful to patients prescribed high doses such as concentrated insulin human regular (U-500).

A number of different aspects of illustrative embodiments are described herein.

1. For example, a system for injecting medicament into a patient comprises an adapter configured to be detachably coupled between an injection pen housing and its needle assembly and to deliver the medicament from the injection pen housing to the needle assembly, a sensor configured as a microchip provided in the adapter to sense at least one characteristic about the medicament or its delivery to the patient and generate sensor data, and a device configured to wirelessly communicate with the sensor to obtain its sensor data.

2. In the system, the device is a portable user interface.

3. In the system, the device is configured to obtain wireless transfer of the sensor data and to provide wireless power to the sensor.

4. In the system, the device employs one of RFID and SAW for providing wireless power to the sensor.

5. In the system, the sensor detects at least one of drug identification, concentration, agglomeration, and degradation, and flow rate.

6. In the system, the device comprises an application for performing at least one of interfacing with the adapter, processing the sensor data, setting alerts relating to the medicament or its delivery, and graphing and indexing information relating to medicament use and degradation for display.

7. Another example system for injecting medicament into a patient comprises: a patch-like infusion device that can be adhered to a skin surface of a patient and comprises a reservoir of medicament and a needle manifold to deliver a designated amount of the medicament from the reservoir to the patient, a sensor configured as a microchip provided in the patch-like infusion device to sense at least one characteristic about the medicament or its delivery to the patient and generate sensor data, and a device configured to wirelessly communicate with the sensor to obtain its sensor data.

8. In the system, the device is a portable user interface.

9. In the system, the device is configured to obtain wireless transfer of the sensor data and to provide wireless power to the sensor.

10. In the system, the device employs one of RFID and SAW for providing wireless power to the sensor.

11. In the system, the sensor detects dose amount.

12. In the system, sensor data can be used to estimate insulin on board and confirm quality of dose.

13. Another example system for injecting medicament into a patient comprises: an infusion set that can be adhered to a skin surface of a patient and is configured to deliver a designated amount of the medicament from a pump to the patient, a sensor configured as a microchip provided in the infusion set to sense at least one characteristic about the medicament or its delivery to the patient and generate sensor data, and a device configured to wirelessly communicate with the sensor to obtain its sensor data.

14. In the system, the device is a portable user interface.

15. In the system, the device is configured to obtain wireless transfer of the sensor data and to provide wireless power to the sensor.

16. In the system, the device employs one of radio frequency identification (RFID) and surface acoustic wave (SAW) technology for providing wireless power to the sensor.

17. In the system, the sensor detects at least one of a site failure, a medication error and compliance.

18. In the system, the sensor is a pressure sensor.

19. In the system, the sensor detects at least one of a site failure, occlusion, and leakage.

The present invention may comprise a method or apparatus or system for injecting medicament into a patient having one or more of the above aspects, and/or one or more of the features and combinations thereof.

BRIEF DESCRIPTION OF THE DRAWINGS

The above and/or other aspects and advantages of embodiments of the invention will be more readily appreciated from the following detailed description, taken in conjunction with the accompanying drawings, in which:

FIG. 2 illustrates a smart pen configuration constructed in accordance with an illustrative embodiment of the present invention;

FIGS. 3A, 3B, 4A, 4B, 5A, 5B, 6A and 6B illustrate advantages of the smart pen adapter system illustrated in FIG. 1;

Throughout the drawing figures, like reference numbers will be understood to refer to like elements, features and structures.

DETAILED DESCRIPTION OF ILLUSTRATIVE EMBODIMENTS

Figures 1A, 1B:
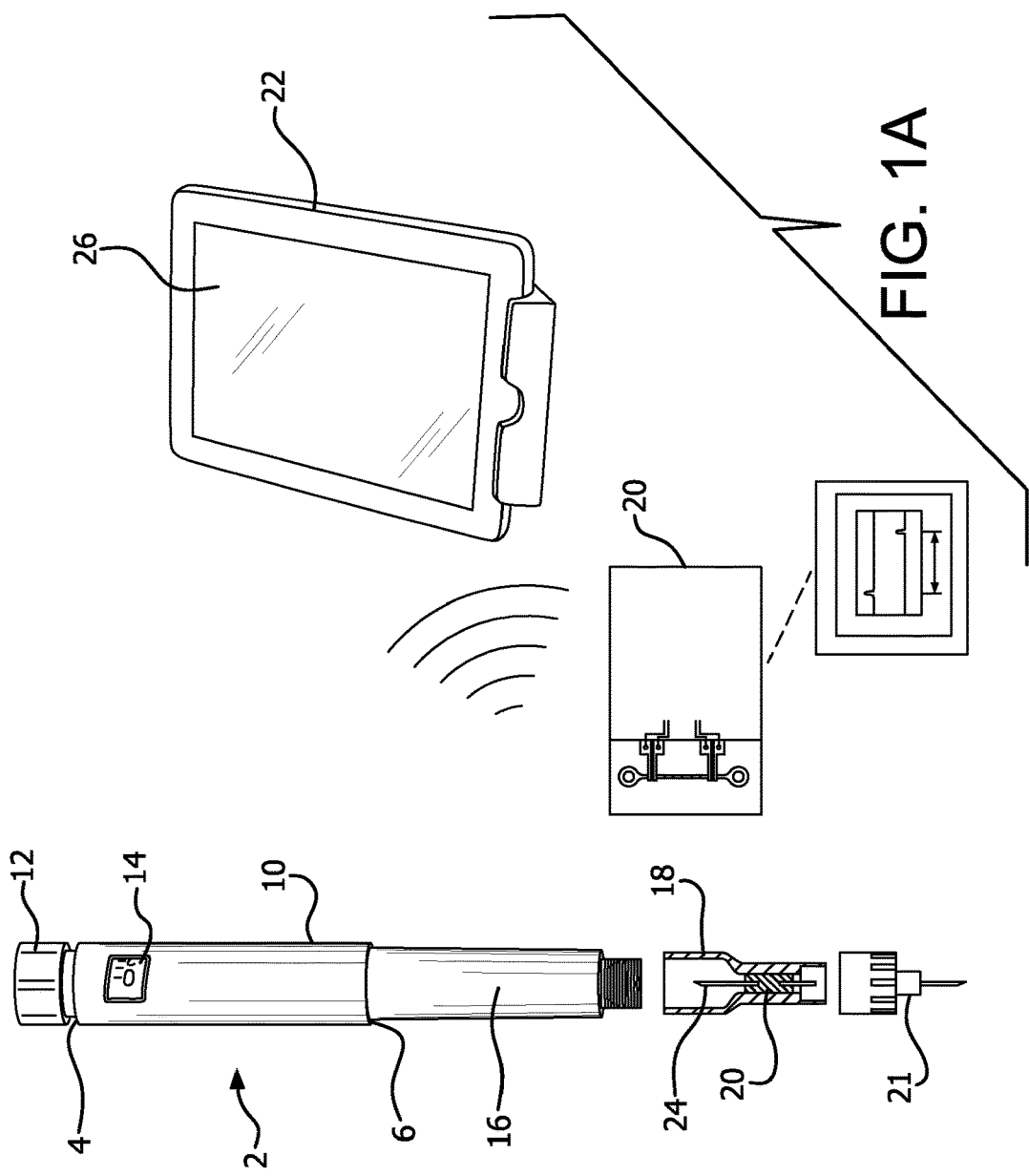
FIGS. 1A and 1B illustrate a smart pen adapter system constructed in accordance with an illustrative embodiment of the present invention.
Figure 3B:
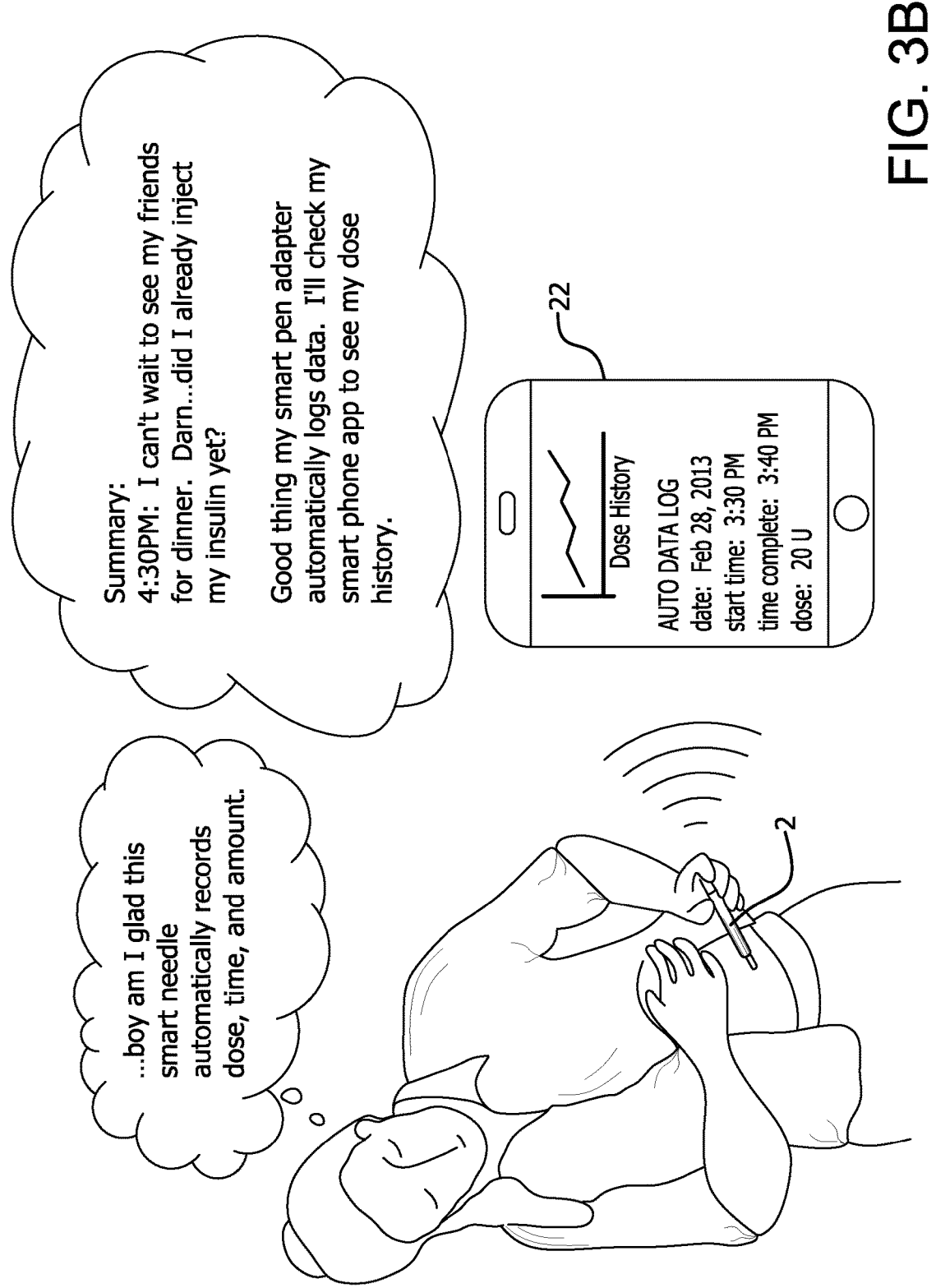

In accordance with an illustrative embodiment of the present invention, FIGS. 1A and 1B illustrate a smart injection pen 2 having dose setting capabilities, and a smart sensor 20 configured to detect information about characteristics and use of the injection pen 2 and wirelessly communicate the information to the pen 2 or a portable device 22. As shown in FIG. 1A, the portable device can be a smartphone or tablet or other portable device such as a laptop or handheld personal data assistant (PDA) such as a personal diabetes manager (PDM) which has a processing device, memory, display, user interface and communications interface. The injection pen 2 includes a housing 10 having a proximal end 4 and distal end 6. A dose dial knob 12 is coupled to the proximal end 4 of the housing 10. The user can set a desired dose by rotating the dose set knob 12 with respect to the housing 10 until the desired dose amount is shown in window 14. Additional drive and dose setting elements are secured within the housing 10 and configured, for example, in a conventional manner with respect to existing drug delivery pens. A cartridge retaining member 16 is secured to the distal end 6 of the housing 10. A cartridge of injectable fluid, e.g. insulin or other medicament, is housed within the cartridge retaining member 16. The cartridge retaining member 16 interfaces with a needle adapter 18 which, in turn, interfaces with a needle assembly 21 for injecting the medicament into a user. Another example delivery pen is described in commonly-owned U.S. Pat. No. 5,931,817, which is incorporated by reference herein.

As shown in FIG. 1B, then pen 2 can have a needle adapter 18 that includes a smart sensor 20, thereby making the needle adapter 18 into a smart pen needle adapter that is configured, for example, to detect or receive and process information relative to the medicament being delivered and to transfer (e.g., wirelessly) sensor information to the injection pen itself 2 or to the portable device 22.

The pen needle adapter 18 can be removably coupled at one end thereof to the cartridge retaining member 16 in a conventional manner such as via threads on the exterior circumference of cartridge retaining member 16 being arranged and dimensioned to cooperate with grooves in the interior circumference of the pen needle adapter 18, or vice versa. Similarly, the pen needle adapter 18 can be removably coupled at the other end thereof to the needle assembly 21 in a conventional manner such as via threads on the exterior circumference of pen needle adapter 18 being arranged and dimensioned to cooperate with grooves in the interior circumference of the needle assembly 21, or vice versa. Other quick-connect interlocking means can be provided to the cartridge retaining member 16, pen needle adapter 18, and needle assembly 21 to allow for coupling and decoupling of these components.

The smart sensor 20 is capable of wirelessly communicating with a portable user interface 22, for example, or pen 2, or both, either of which can display various features and characteristics of the medicament injection process (e.g., on the touchscreen of a smartphone or LED screen of a PDM or on the display 14 of the pen 2). As stated above, the user interface 22 can be a mobile phone or other hand-held or portable device. The user interface 22 can include applications specific to processing and/or interfacing with the smart pen needle adapter 18, such as setting alerts, graphing and indexing information related to use and/or degradation of the drug delivered by the injection pen with smart pen needle adapter 18. The user interface 22 can also enable a user to manipulate or configure or simply view different desired characteristics to be processed by the smart pen needle adapter 18 such as sensing volume or mass flow rates or pressure to determine leakage or occlusion or incomplete drug delivery, or constituent, diluent, temperature to determine drug degradation or expiry or incorrect drug, and so on, depending on the type(s) of the sensor(s) 20 provided in the pen needle adapter 18. The smart pen needle adapter 18 can communicate with the user interface 22 or pen 2 via radio frequency (RF) wireless communications such as Bluetooth®, Zigbee®, 802.11, or other conventional wireless solutions such as RFID or SAW technology described below in connection with US 2008/0129475 to provide wireless power (e.g., via an inductive link) and as well as communications. The smart pen needle adapter 18 and the user interface 22 can also employ line-of-sight communication such as using infrared (IR) technology used by some medical devices. Wireless communication systems, since they do not require a line of sight, are preferred over IR technology. Additionally, the injection pen case or housing 10 can also include a smart sensor 20 (not shown) that can sense use trends, dates of use and remaining cartridges and/or uses. Utilizing the smart sensor, the injection pen 2 case or housing 10 can communicate its detected information to the user interface 22 via wireless communication in a similar manner as discussed above with respect to the smart pen needle adapter 18.

The smart pen needle adapter 18 or other drug delivery-related device configured with a sensor 20 can be configured to detect one or more of a drug identification, concentration, agglomeration, degradation and/or other drug or delivery characteristic using corresponding drug delivery sensing technology that can be coupled to or retrofitted onto injection pen injectors and/or drug delivery cartridges and/or or infusion sets, thereby enabling these pen injector systems or drug delivery cartridges or infusion sets to stop medication errors that occur primarily through self or automated injection or other self-administrating drug delivery device (e.g., as opposed to bench-top fluid testing systems in pharmacies or IV fluid testing systems deployed in a clinical setting with IV poles supporting pumps and cannula extending therefrom). One example, which is used throughout this description, is insulin delivery. It is to be understood, however, that illustrative embodiments of the present invention could be applied to any drug delivered through an injection pen needle or drug delivery cartridge or infusion set or patch.

As stated above, no insulin pump or injection pen needle currently has the capability to accurately and scientifically (e.g., through sensing technology) verify the drug being administered, dose, and/or flow, and/or catch medication errors due to drug expiration, contamination, incorrect dosing, and so on.

In accordance with illustrative embodiments of the present invention, smart drug delivery device (e.g., a smart drug container, or smart injection pen needle adapter 18, or smart cannula, or smart infusion set) provides accurate scientific verification and/or detection and/or identification of one or more of the following parameters or characteristics of drug administration such as, but not limited to, temperature, contamination, drug manufacturer, compromised drugs (e.g., due to light exposure, improper handling, contaminated or faulty containers, tampering, temperature exposure, or expiry from actual drug deterioration which is more accurate than projected expiry based on date of preparation), time of injection/infusion(s), drug, dose, diluent, concentration, or agglomeration. The smart drug delivery devices of the illustrative embodiments also provide convenient and wireless access to stored data such as, but not limited to, use by date, medication storage device information (e.g., catalog information and/or lot number), patient information (e.g., one or more of height, weight, gender, ethnicity, allergies, conditions), patient's electronic medication administration record (eMAR) downloaded from hospital information technology (IT) system, drug use conditions, dates of preparation or device access, and/or drug information (e.g., lot number, manufacturer), as well as actions/alerts such as, but limited to, visual or audible cues if the drug should not be administered, documentation (e.g., information automatically provided to the patient's medical record or the doctor's office), potential display of information about contents and delivery instructions and a locking mechanism if drug should not be delivered for any reason.

As stated above, to ensure the proper delivery of insulin or drug, there are many different types of drug pumps. These different drug delivery technologies have documentation technologies, patient information technologies and some alerts to let the patient know if something is wrong. Most pumps, for example, can also be programmed for the specific user. Some devices, for example, have a PDM, which is a wireless, hand-held device that is used to program the drug delivery device with customized insulin delivery instructions, that monitors the operation of the drug delivery device, and checks blood glucose levels. In accordance with illustrative embodiments of the present invention, the sensor 20 can be used in conjunction with injection pen needles or other pen components (e.g., cartridge retainer member 16), or drug cartridges, or infusion set, or cannula, or any insulin pump or other portable drug delivery device operated or wearable by a user for self-administration of a drug.

The sensor 20 can be, for example, a fluid detection sensor, and used with or without identification data repository (IDR) or container identification data repository (CIDR) data or other stored data (e.g., as exemplified in the preceding paragraph) embedded in a radio frequency identification (RFID) chip, for example, and provided to any injection pen needle/device or a drug delivery cartridge. The example sensing technologies described herein can be powered by the pump to which the cartridge attaches or could be independently powered by a small battery or a surface acoustic wave (SAW) (e.g., inductive field energy or radiation field energy).

The fluid detection sensor 20 is in contact with the fluid so that it can identify important characteristics of the drug. As mentioned above, it can detect the drug, dose, diluent, manufacturer, concentration, and whether the drug has been compromised, expired, contaminated or should not be delivered to the patient, among other characteristics.

When the sensor technologies (e.g., IDR or CIDR data on RFID chips, and fluid detection sensor) are embedded into a pump, for example, the sensor 20 can signal the pump to stop the injection or create a visual or audible display for the patient or clinician to alert them of a complication (e.g., occlusion, leak, incorrect dose or drug, expiry or contamination). For example, the drug cartridge provided to the pump can have an CIDR chip and its information interrogated by a controller in the pump to obtain drug identification, manufacturer, lot number, catalog number, expiration date and other information that would alert the pump controller of an incorrect drug, dose, concentration or drug expiration. Since it has a flow rate detector, the sensor 20 can also provide a feedback mechanism to the pump to ensure the correct flow rate. If there was an occlusion or leak, or the connection to the patient was compromised, or the pump has stopped, the sensor 20 can detect these conditions and operate in conjunction with the user interface 22 to generate an alert to the pump user to check the infusion line. In all embodiments of the present invention, drug administration, and any errors that occur during drug administration, can be documented and reported to a mobile device or computer (e.g., to the user interface 22 which can in turn communicate this information to any other networked device) to alert the pump user's doctor's office, caregiver, or other stakeholder besides the patient to any problems or complications that arise. Alternately, the data can be stored on the device (e.g., in a memory provided in the housing 10 of a pen 2, or in a pump, or in a user interface 22 connected wirelessly or via cable to the drug delivery device) and accessed later for the drug administration history.

A biosensor (e.g., a blood glucose meter (BGM) or continuous blood glucose (CGM) meter wirelessly connected to a pen 2 or pump 102 or patch pump 90) can also be employed to monitor the blood glucose levels or other physiologic conditions to ensure that the optimal dose was given to the patient. This biosensor can be configured to provide a feedback mechanism to a drug delivery system and, as such, adjustments to drug delivery can be made without any human interactions. The biosensor or drug delivery system can also communicate with an IDR (e.g. via an 802.11 network connection), or retrieve information from an IDR RFID chip (i.e., if present locally such as provided in a cartridge) to determine the real time flow rate and/or dose that was prescribed, and then it can adjust the dose and any changes to the flow rate or dose can be confirmed by the fluid detection sensor 20. The stored IDR data can contain, for example, patient information (e.g. one or more of height, weight, gender, ethnicity, allergies, conditions, etc.), drug, dose, diluent, concentration, lot number, manufacturer, among other information exemplified above. The sensor can also have temperature and/or light exposure history. If the sensor is embedded into the cartridge, a CIDR RFID chip can allow for the storage of the information about the fluid container such as manufacturer, lot number, catalog number, expiration date (if relevant), etc.

The sensor 20 can use impedance spectroscopy as the fluid detection mechanism, as described by patents supplied by S.E.A. Medical Systems, Inc. (e.g., US 2010/0305499). However, other sensing techniques can include, but are not limited to, optical, electrical, mechanical, thermal and/or rheological, or a combination of which could provide enough fluid characterization mechanism to readout the necessary drug information. This multiparametric approach has been documented by S.E.A. Medical Systems Inc. in the afore-mentioned patent. For example, S.E.A. Medical System Inc.'s IV sensing technology has been leveraged by illustrative embodiments herein for detection of one or more of insulin contaminants, degradation, dose, diluent and flow rate at a self-administration drug delivery device as illustrated, for example, in FIGS. 1, 9, 10*a* and 11.

There are some techniques used currently to power wireless sensors such as providing wireless power inductively, through radio frequency energy transfer, or capacitively as described in U.S. Patent Application Publication No. 2008/0129475 A1. In this patent, RFID or SAW are recommended for sensor powering. One of these techniques could be used to provide enough power and signal amplification to allow the wireless transfer of information from the smart sensor 20 or 180 to the interrogator in the drug delivery device in which sensor is deployed (e.g., a controller in the pen 2 or pump 102 or other device, or the user interface 22). There are two patents that have been identified which employ an RFID chip embedded in a syringe (US 2009/0322545 and WO 2009/025996A1); however these patents do not incorporate fluid sensing as described herein with reference to illustrative embodiments of the present invention.

FIG. 2 illustrates a smart injection pen 2 having RF (e.g., Bluetooth®) communication abilities and information processing capabilities. However, a smart injection pen 2, as shown in FIG. 2, can also be retrofitted to receive the smart pen needle adapter 18 in order to add additional sensing abilities not previously realized in the smart injection pen. For example, the smart pen needle adapter 18 can identify if the injection pen 2 itself is malfunctioning or if the dosages being administered to the user are inconsistent with the dosage settings on the injection pen. These additional features, as well as the additional features described above, enable a user to easily upgrade a smart injection pen to improve performance and provide the user with additional important information. In addition to generating reminders to a user of time to dose, the pen 2 can also communicate (e.g., wirelessly) with a BGM or CGM or other automated blood glucose testing device to improve glucose control by recommending insulin dosing with greater accuracy (e.g., using feedback information from glucose testing provided by the BGM/CGM), recording actual dosing information (e.g., as confirmed by a flow or other type of sensor 20 provided in a pen needle adapter and configured to accurately detect amount of drug actually delivered), and integrating with eHealth options (e.g., automatically reporting test information and dose information to a patient's electronic health record) to automate compliance with a prescribed diabetes management protocol. Such automated sensing, feedback and adjustments to recommended insulin dosing eliminates manual blood glucose control regimens and their intrinsic inaccuracies due to relying on patients to manually track intake of carbohydrates (i.e., carb counting) and perform insulin calculations, which result in dosing errors. With a smart drug delivery device 2, patients spend significantly more time within their recommended range for glucose control, which can result in HbA1c improvement.

FIGS. 3A, 4A, 5A and 6A illustrate difficulties and disadvantages to using conventional insulin/medicament injection devices (e.g., a pen 3) without smart sensors 20, 180 as described herein, particularly amidst everyday activities. FIGS. 3B, 4B, 5B and 6B illustrate how a smart needle adapter, for example, smart needle adapter 18 in a pen 2 or other drug delivery device having one or more smart sensors 20, 180 as described herein, overcomes the difficulties of and disadvantages of conventional injection devices and provides additional features previously unavailable with conventional injectors.

Figure 5A:
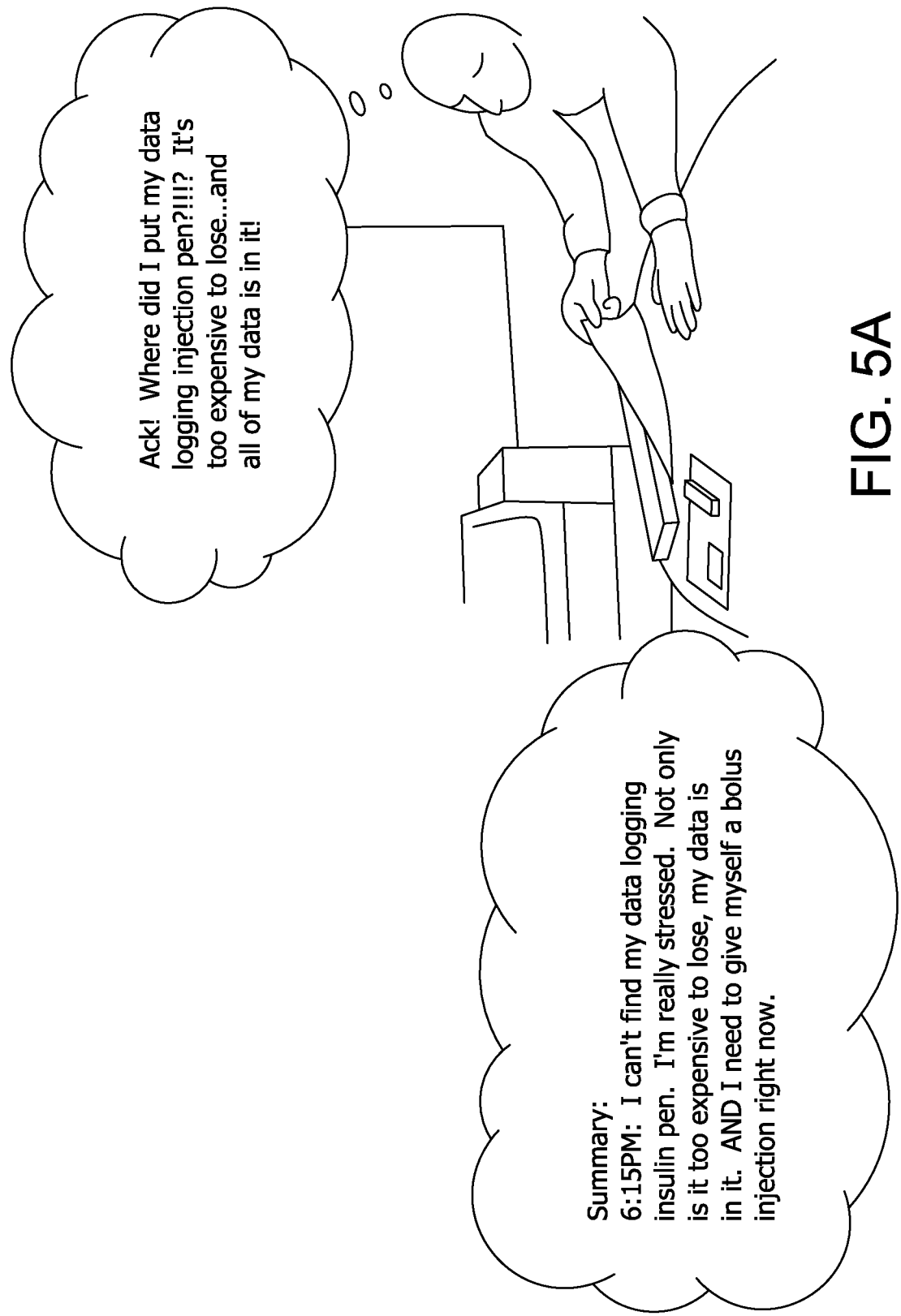
Figure 6A:
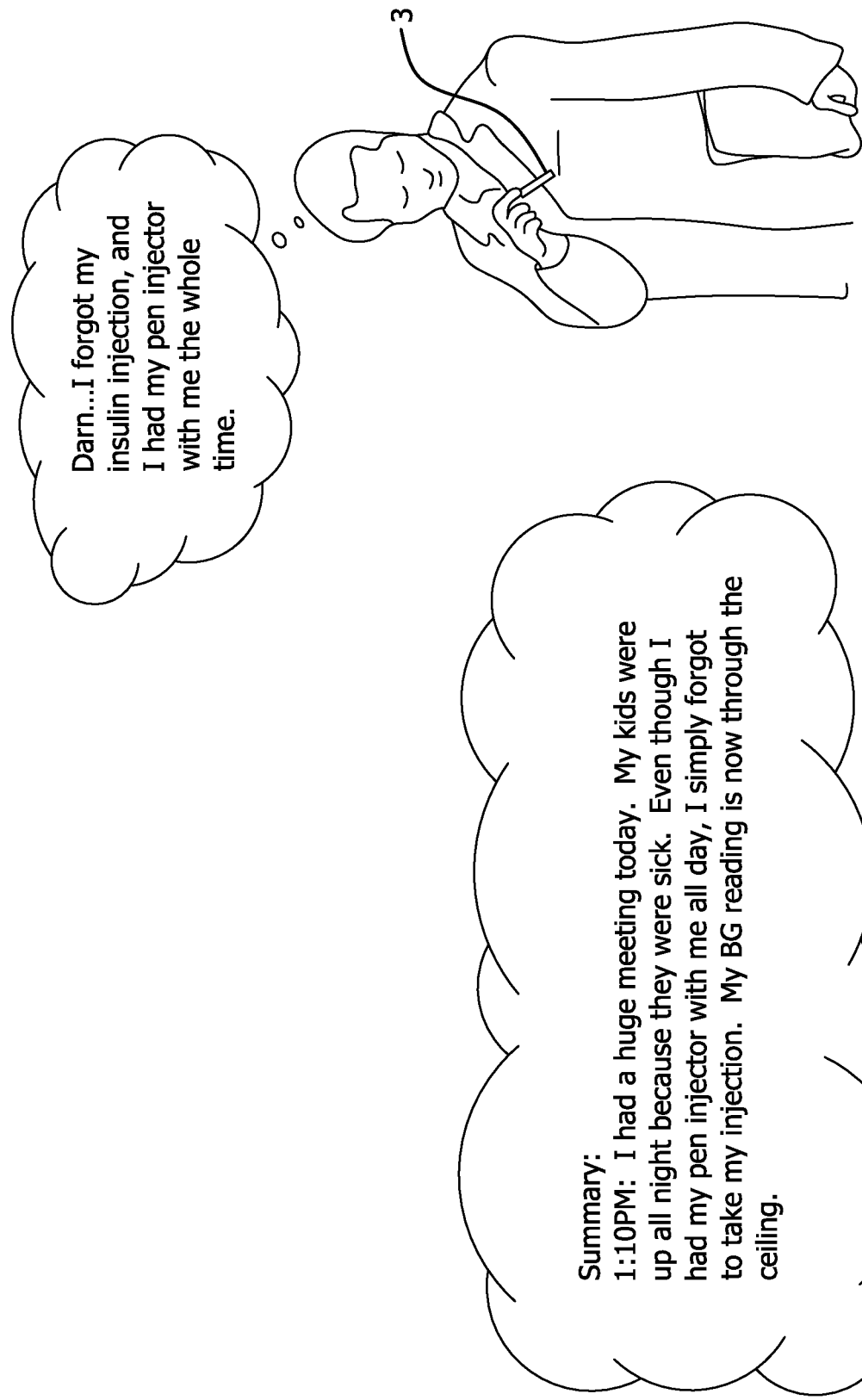

With reference to FIG. 3A, users of conventional insulin pens 3 often must set the dose (e.g., via a dose dial knob) and, if their pen does not log an injection event, they must manually record their insulin administration events. As illustrated in FIG. 4A, these users also receive no feedback regarding whether the insulin is the correct drug prescribed, whether the insulin is viable and not degraded, or whether the dose was correct, timely and complete. With reference to FIGS. 5A and 6A, many users of conventional injection pens 3 also receive no alerts of when to dose, nor do they have convenient access to their insulin management data apart from what may or may not be logged by and stored at their pen 3.

Unlike existing pens 3 described with reference to FIGS. 3A, 4A, 5A and 6A, smart drug delivery devices (e.g., pen 2 or pumps 90, 100) employ smart sensors 20,180 and connectivity with a user interface 22 to provide valuable infomatics to users as illustrated, for example, in FIGS. 3B, 4B, 5B and 6B. For example, with regard to FIG. 3B, a smart pen 2 can have a sensor 20 for sensing flow to confirm total dose actually delivered. The sensor data is available, for example, to the pen 2 and/or user interface 22, either of which can interrogate the pen needle adapter 18 with smart sensor 20 periodically and/or after sensing an event such as dose dial-in or activation of insulin injection, and associate time stamp data with received sensor data and determine such parameters as time and amount of dose delivered. Thus, the smart pen needle adapter 18 facilitates data logging and data integration to provide a user with convenient access to accurate information on a user interface 22 screen to see current dose amount, time of dose and dose information relative to previously stored, historical insulin administration events.

Figure 4B:
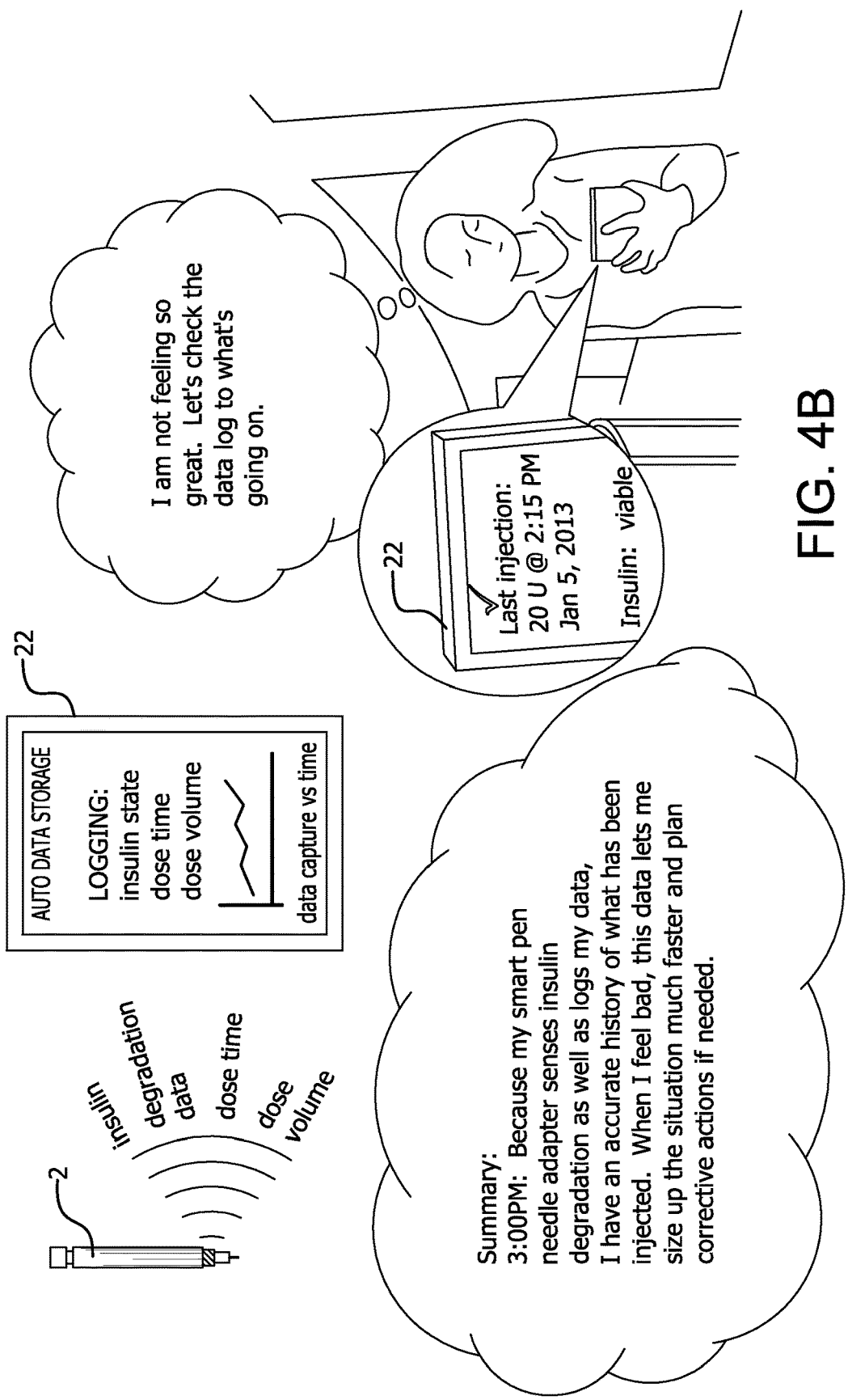

With reference to FIG. 4B, the pen 2 has a smart sensor 20 in an adapter 18 or in a cartridge, connectivity with a user interface 22 such as a smartphone or laptop or PDM, and stored (or access to stored) historical insulin administration events (e.g., at the pen 2 or user interface 22) such as dose volume, dose time, insulin identification and viability, which permits a user to conveniently access and consider a body of injection information to more quickly determine where changes in a diabetes management protocol may be needed or where patient-compliance has been lacking such as not injecting at prescribed times or using degraded or contaminated insulin. As described herein, sensor(s) 20 can be provided in the drug delivery device (e.g., pen needle adapter 2, or in insulin cartridge, or in patch pump 90, or within or in connection with an infusion set 100) to monitor temperature of insulin, concentration, impedance spectroscopy signature (e.g., to detect degradation) and the like.

Figure 5B:
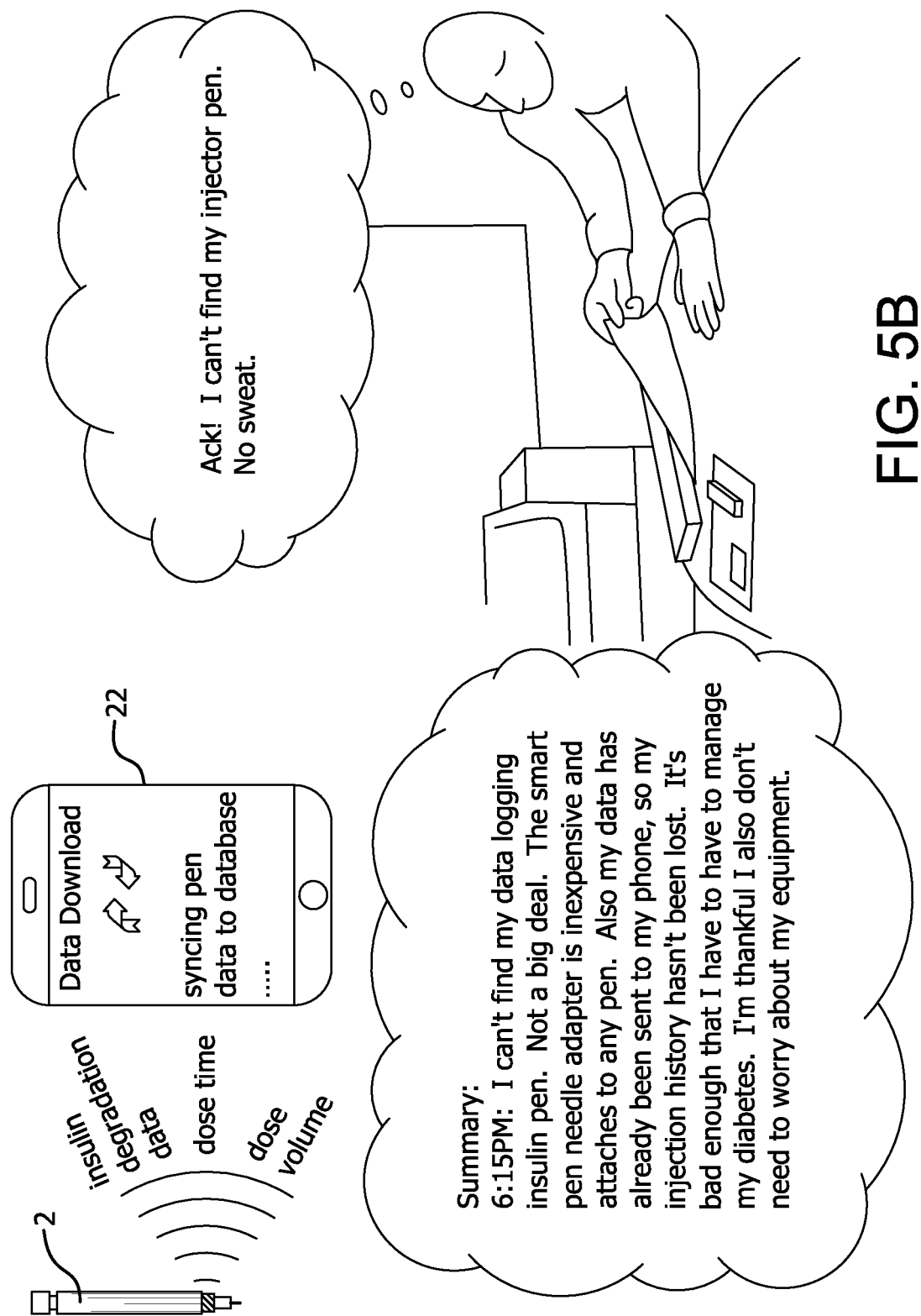

With reference to FIG. 5B, sensing, storing and improving insulin delivery data via smart sensors 20, 180 and wireless connectivity as described herein realizes a number of advantages over conventional drug delivery devices such as pens 3. For example, the smart sensor 20 can be provided, for example, in an inexpensive pen needle adapter 18 that can be attached to any pen injector to harvest considerably more information about a dosing event than is available from a pen 3. For example, a pen 2 having a pen needle adapter 18 with smart sensor 20 can detect actual dose delivered, volume, concentration, and/or degradation and share sensor information with the controller in the pen 2 and/or user interface 22 to give a rich injection history database that can be synchronized in the user interface 22 for more convenient access and manipulation and redundancy.

Figure 6B:
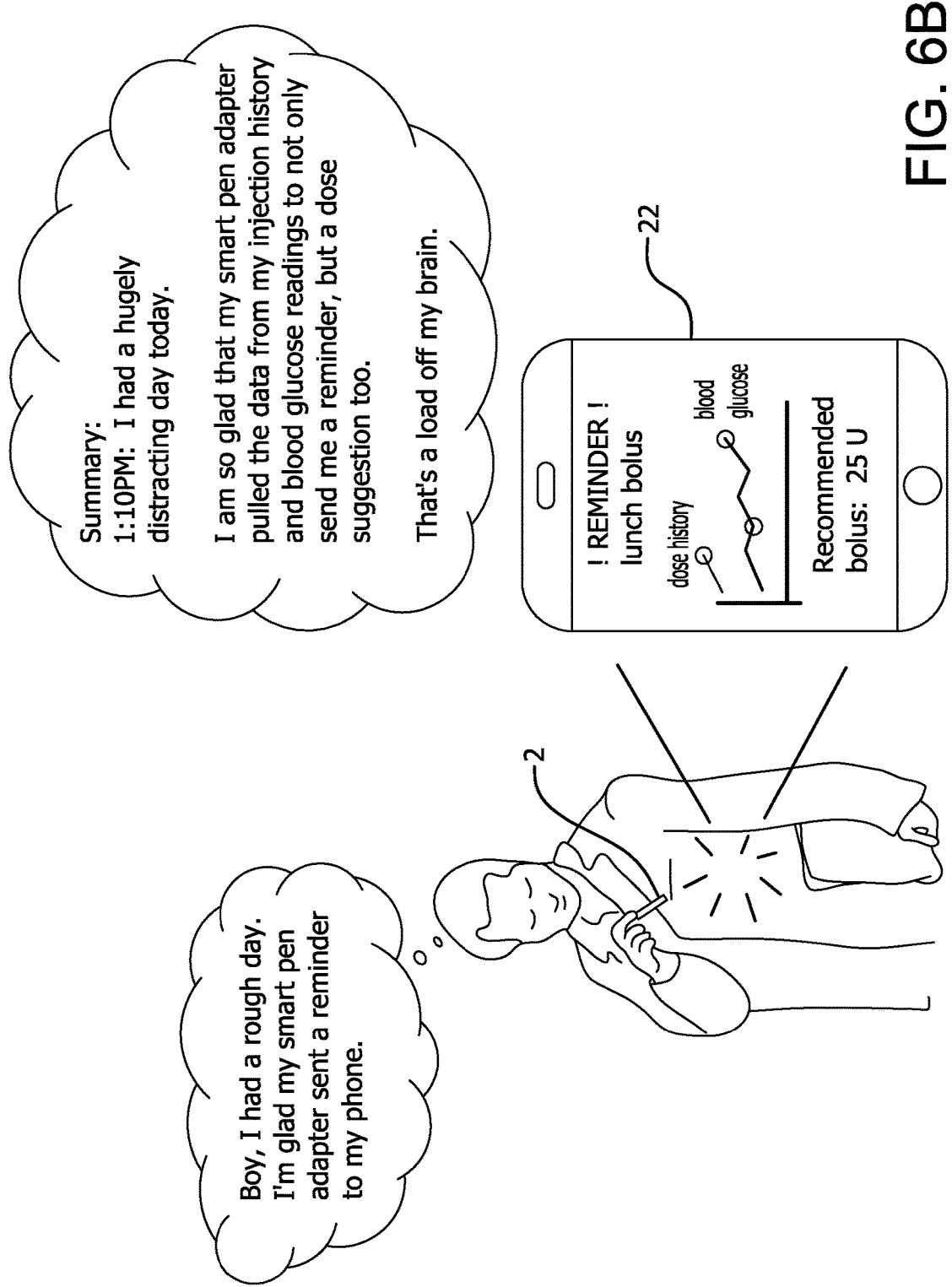

With reference to FIG. 6B, a pen 2 having a smart needle adapter 18 and/or a user interface 22 can be wirelessly coupled to a biosensor such as a BGM/CGM, as stated above, to receive historical glucose data as well. Glucose control can therefore be improved since the pen 2 and/or a user interface 22 can provide recommendations for insulin dosing having greater accuracy (e.g., using feedback information from glucose testing provided by the BGM/CGM), and record actual dosing information (e.g., as confirmed by a flow or other type of sensor 20 provided in a pen needle adapter and configured to accurately detect amount of drug actually delivered).

Another embodiment of the present invention is patch-like infusion or self-injection device 90 to deliver a pre-measured dose of a substance, such as a liquid drug or medication, to a patient over a period of time or all at once. The device is preferably provided to the end user in a pre-filled condition, that is, with the drug or medication already in the device reservoir.

Figure 7:
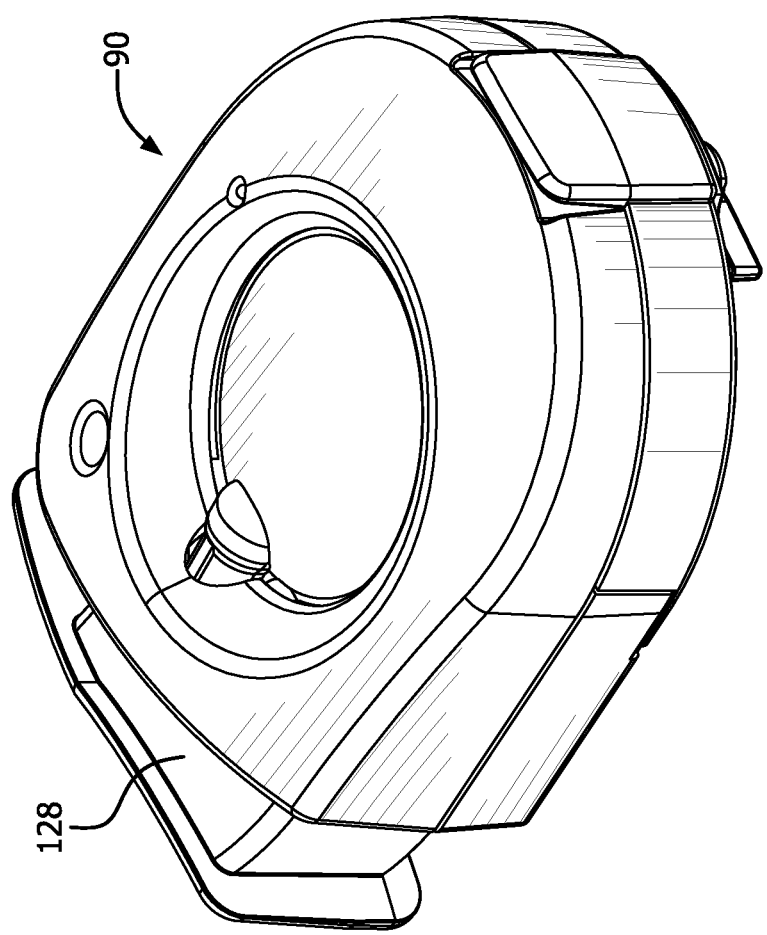
FIGS. 7-9 illustrate a smart infusion device constructed in accordance with an illustrative embodiment of the present invention.
Figure 8:
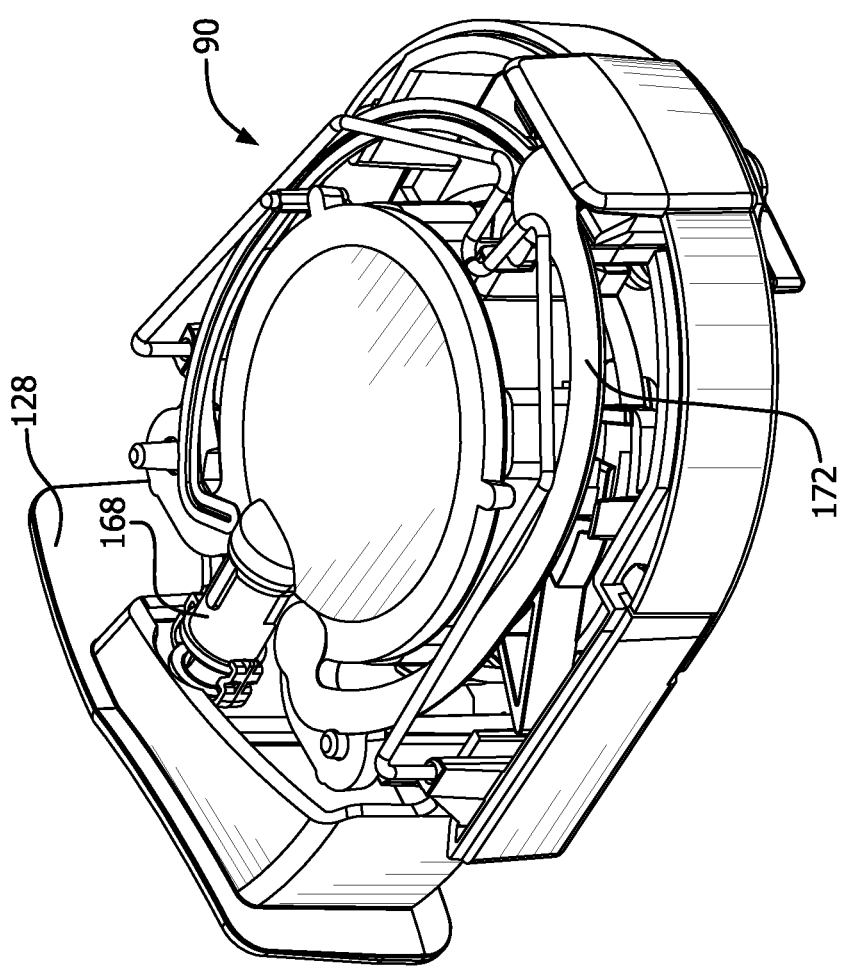
Figure 9:
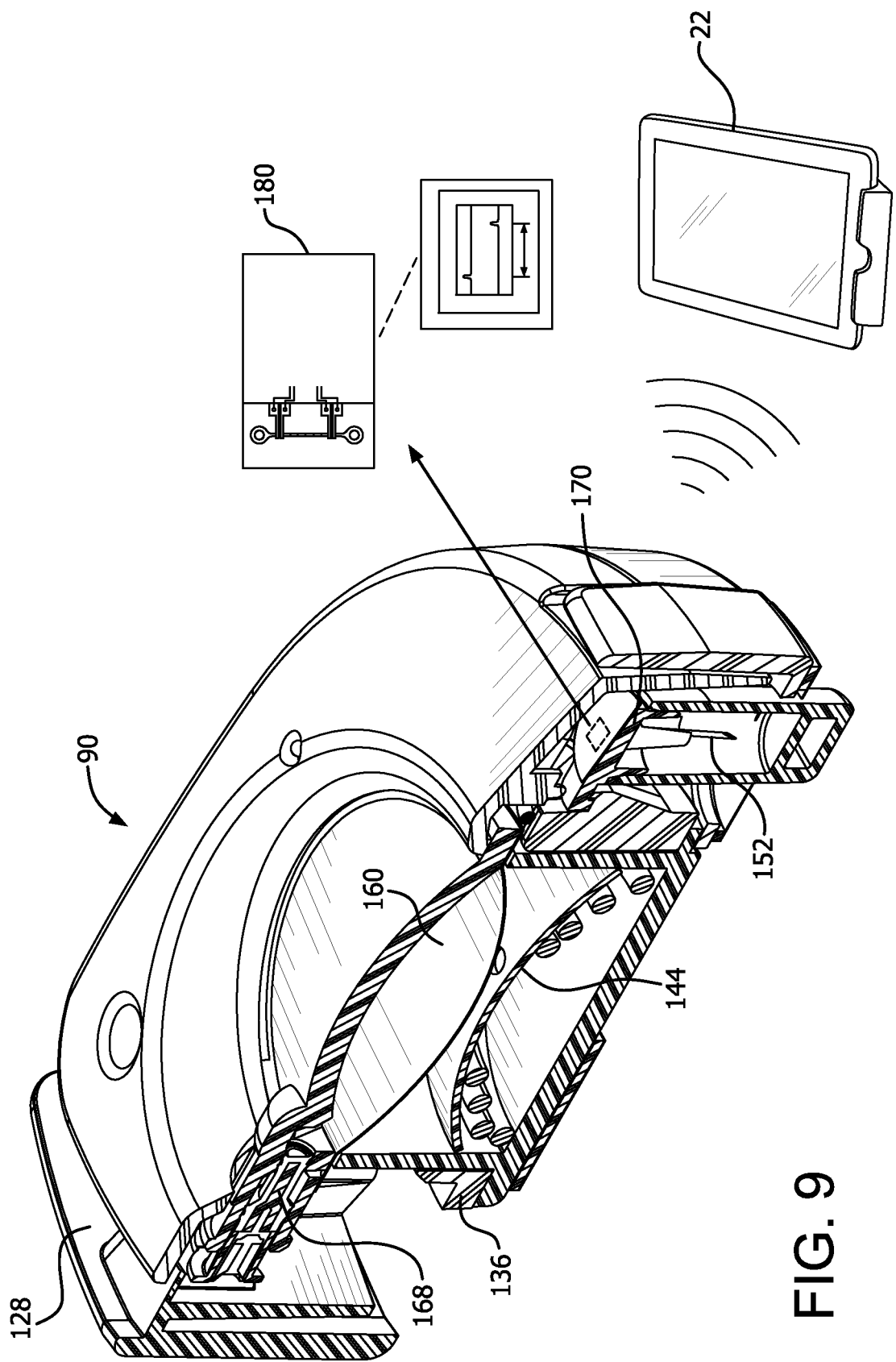

The patch-like infusion device 90 of FIGS. 7-9 is self-contained and is attached to the skin surface of the patient by adhesive disposed on a bottom of the infusion device 90 (as will be described in greater detail below). In accordance with an illustrative embodiment, the infusion device 90 can be configured and to operate as described in commonly-owned WO 2011/075101, which is incorporated herein by reference. Once properly positioned and activated by the patient, the pressure of a released spring on a flexible reservoir within the device can be used to empty the contents of the reservoir through one or more patient needles (for example, microneedles) via a needle manifold. The substance within the reservoir is then delivered through the skin of the patient by the microneedles, which are driven into the skin. It will be understood that other embodiments are possible in which the spring is replaced with a different type of stored energy device, which may be mechanical, electrical and/or chemical in nature.

The activation and energizing of the infusion device 90 that is accomplished in a single multi-function/step process can include depression of an activator button 128 by a patient, and rotation of a rotor 136 due to engagement between an activation arm of the activator button 128 and an activation projection of the rotor 136. The rotation of the rotor 136 rotates and releases the plunger 144 to pressurize the fluid within the reservoir 160. Additionally, the rotation of the rotor 136 releases a drive spring from a drive spring holder, thereby driving a needle manifold 170, which secures microneedles 152, such that microneedles 152 extend outside of the infusion device 100. The single multi-function/step process also includes movement of the valve 168 from the pre-activated position to the activated position due to the activator button 128 engaging and moving the valve 168 when the activator button 128 is depressed, thereby commencing fluid flow between the reservoir and the microneedles 152 via the channel 172.

A smart sensor 180 (e.g., similar to the sensor 20 described above) can be secured with respect to the needle manifold 170 to accurately and efficiently detect dose recording, timing and amount, insulin remaining in the reservoir 160, dose reminders, dosing suggestions (based on bolus calculators and automated BG data input), missed dose alarms, insulin on board estimation, cross-communication with BG sensors (episodic and continuous), data integration (BG+dosing) storage and display, data communication (patient PC, HCP, e-health management systems) and confirmation of dose quality (e.g. leakage). For example, the sensor 180 can be coupled at a point along a cannula or other fluid throughway from the reservoir 160 to the needle (e.g., microneedles 152). Alternatively, the sensor 180 can be provided in the reservoir 160 depending on the type of sensor.

The smart sensor 180 is configured to wirelessly communicate with a portable user interface 22 (e.g., a pump or PDM or other user interface 22) which displays various features and characteristics of the medicament injection process. The user interface 22 can also enable a user to manipulate or configure different desired characteristics to be processed by smart sensor 180. The smart sensor 180 can communicate with the user interface via radio frequency (RF) wireless communications such as Bluetooth®, Zigbee®, 802.11, or other conventional wireless solutions such as RFID or SAW technology described above in connection with US 2008/

0129475 to provide wireless power (e.g., via inductive field energy or radiation field energy) as well as communications. Some medical devices communicate via a line-of-sight using infrared (IR) technology. Wireless communication systems, since they do not require a line of sight, are preferred over IR technology.

The smart sensor 180 or 20 is one or more of a drug identification, concentration, agglomeration, and degradation sensing technology that can be coupled to or retrofitted onto infusion devices and/or drug delivery cartridges, enabling these infusion devices 100 or drug delivery cartridges described above to stop medication errors that occur primarily through self or automated injection. One example, used to describe throughout this invention is insulin delivery, however, this technology could be applied to any drug delivered through an injection pen needle or drug delivery cartridge or infusion set. These additional features, as well as the additional features presented previously, enable a user to easily upgrade a smart injection pen or infusion set to improve performance and provide the user with additional important information.

Figure 10A:
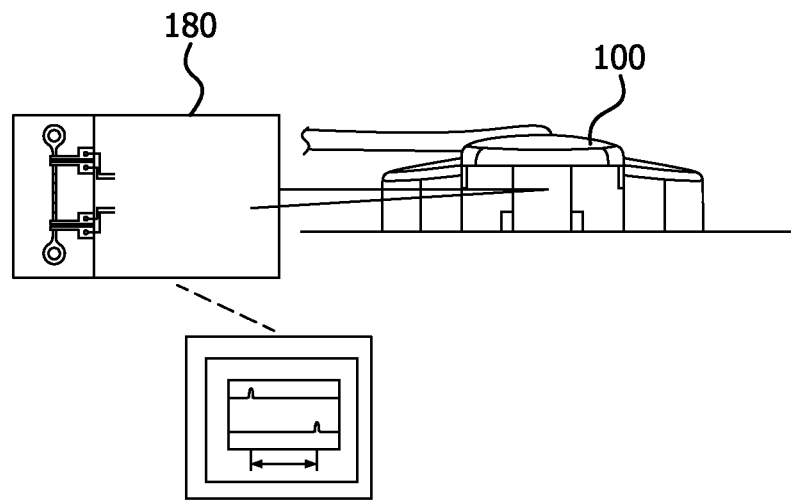
FIGS. 10A and 10B illustrate a smart infusion set and delivery system constructed in accordance with an illustrative embodiment of the present invention.
Figure 10B:
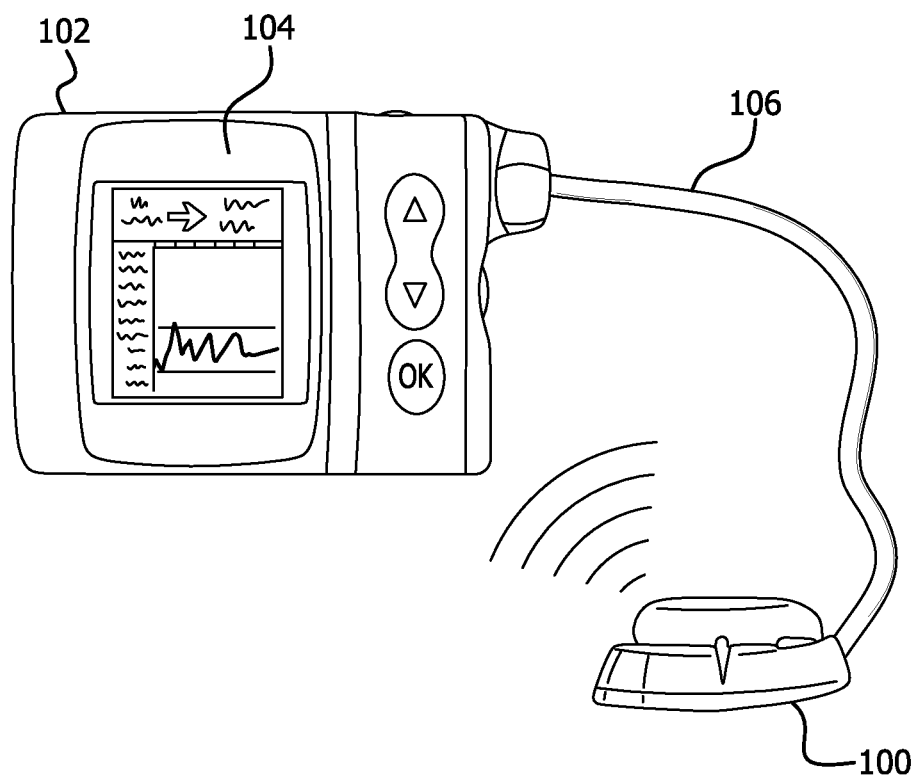

FIGS. 10A and 10B illustrate an integrated smart sensor 180 in a standard infusion set 100 that operates in conjunction with an infusion pump 102. The integrated smart sensor 180 provides sensing capabilities to the improved infusion set 100 for early detection of site failures, medication errors and compliance. The smart sensor 180 can also provide the additional sensing and processing capabilities provided by the sensor 20 in the smart pen needle adapter discussed above. For example, providing smart sensors 20, 180 and related sensing capabilities in or with respect to infusion devices can allow for early detection of site failures, medication errors and compliance, thereby realizing (1) real-time detection and feedback loops for infusion site failures (e.g., leakage, occlusions, insulin instability) and insulin delivery, and (2) improved safety (e.g., via early detections of drug and/or delivery parameters as described herein that can prevent hyperglycemic or hypoglycemic events), both of which have previously been unmet needs for users of conventional self-administered drug delivery devices.

Figure 11:
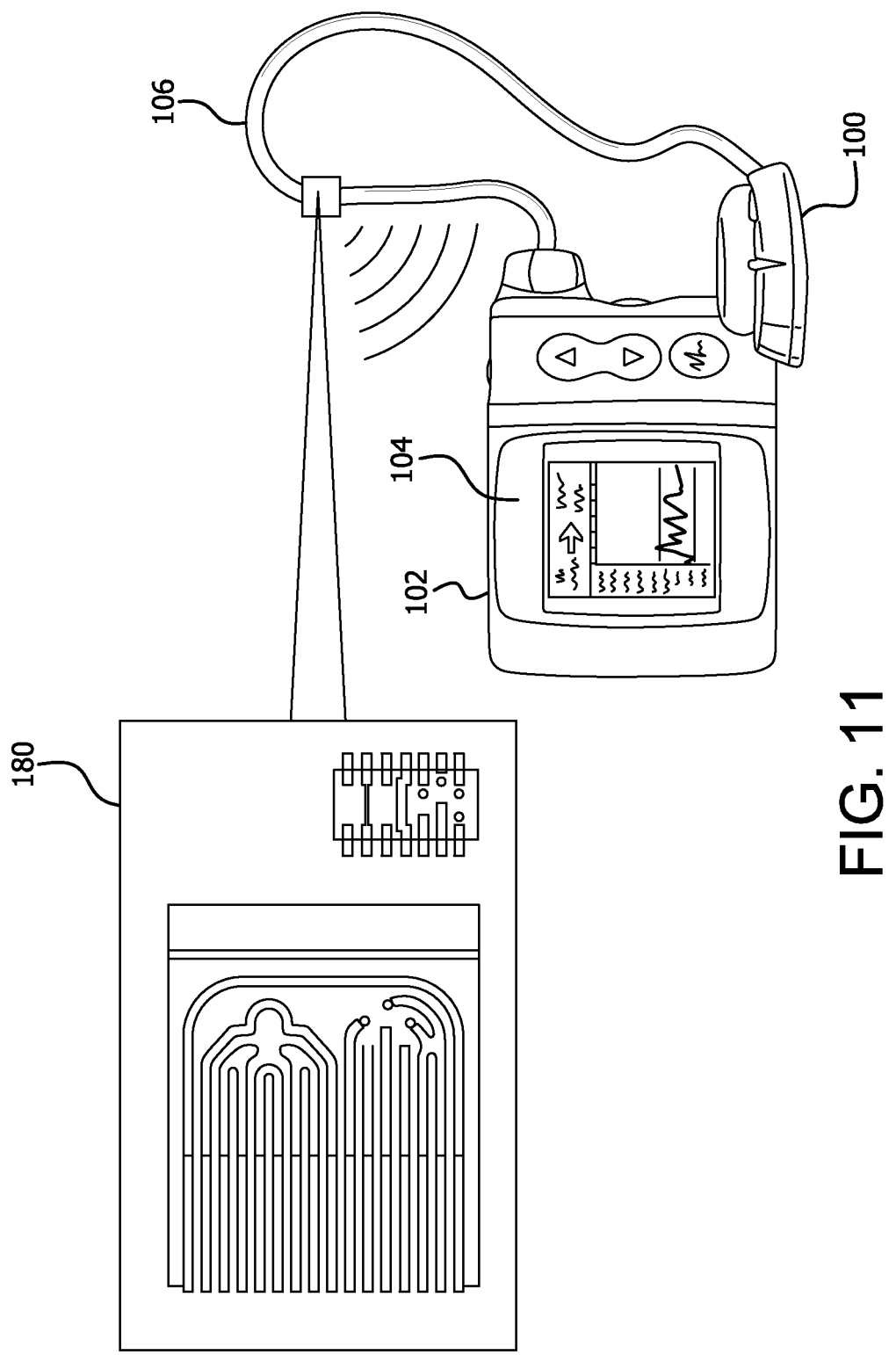
FIG. 11 illustrates a smart infusion system constructed in accordance with an illustrative embodiment of the present invention that can comprise one or more smart pressure sensors for drug delivery site failure detection in accordance with illustrative embodiments of the present invention.

FIG. 11 illustrates a smart pressure sensor or other type of smart sensor 180 that can be incorporated by any of the smart sensors 20, 180 mentioned previously with regard the smart pen needle adapter 18 and integrated smart sensor infusion set 90. The sensor 180 can, for example, be provided in the pump 102 or along the cannula 106 connecting the pump to the infusion set 100 or in the infusion set 100. The smart pressure sensor 180 can, for example, detect site failure, real time occlusion detection and leakage detection. Data from a relatively inexpensive pressure sensor 180 placed close to an injection site for real-time occlusion detection can be used, for example, in conjunction with a flow interruption detection algorithm at a controller in the pump 102 or user interface 22, which in turn can generate an alarm to alert the user of the occlusion. The sensor pressure data can also be used with a leakage detection algorithm based on pressure profiles by a controller in the pump 102 or user interface 22 to determine if leakage has occurred.

In general, the pump 102 includes a drug reservoir not shown that interfaces with a pump device via a displaceable member that may be, for example, a piston, diaphragm, bladder, or plunger. In use, the drug reservoir is filled with a liquid drug, and pressure generated by the pump device moves or expands the displaceable member to push the drug out of the reservoir and into a cannula 106 connected to an outlet of the drug reservoir. The cannula 106 conducts the liquid drug to an infusion set 100, and may be made of substantially impermeable tubing, such as medical-grade plastic. The infusion set 100 comprises a catheter that is fluidically connected to the cannula 108 and delivers the drug to a subcutaneous tissue region on patient.

In accordance with example embodiments, a smart sensor 180 can be placed in the infusion set (e.g., at a selected point within the infusion set 100 between an inlet for the cannula 106 and the catheter) or can be placed along the cannula 106 at an external point thereon between the pump 102 and the infusion set 100. The sensor 180 can be, for example, a microelectromechanical system (MEMS) fabricated sensor or other micromachined chip or microfluidic device having dimensions that can be accommodated in an infusion set 100, for example. The sensor can detect, for example, flow rate or pressure. Sensor data can be collected by the pump 102 or other user interface device 22 that is wirelessly connected to the infusion set, for example, using Bluetooth® or near field communication signals to power the sensor as well as collect its data (e.g., to wake up the sensor and collect data via the communication signals and associated inductive coils).

Feedback from the sensor 180 (e.g., located internally or externally with respect to the infusion set 100) may be used in combination with a drug-delivery protocol pre-programmed in the pump 102 to monitor drug delivery and compensate for external influences that may affect the infusion rate despite unchanged pump device operation (e.g., external condition such as backpressure from the infusion site or clogging of the cannula 106 or infusion set 100). For example, signals from a flow sensor 180 deployed along the cannula 106 (e.g., in the cannula 106 or in a fluid measurement chamber connected to the cannula 106 and indicated generally as "180" in FIG. 11) or in the infusion set 100 (e.g., indicated generally as "180" in FIG. 10A) may be used in conjunction with a processor in the pump 102 or a user interface 22 to determine when the proper dosage has been administered (e.g., determining total dose by integrating flow rate over time relative to a clock associated with the controller, or simply a time stamp when the pump ceases a particular delivery action), to assess the flow through the cannula 106 as reported by a flow sensor 180 and take corrective action if the flow rate deviates sufficiently from a programmed or expected rate (e.g., increase pump driver such as increase the current to the electrolysis electrodes of an electrolysis-type pump to accelerate gas evolution in the electrolysis chamber if the processor determines that a higher flow rate of drug is needed, or decrease the current to the electrolysis electrodes or otherwise decrease actuation of the pump, depending on the type of pump, if the processor determines that a lower flow rate of drug is needed).

As stated above, the sensor 180 can have flow sensing and/or pressure sensing. Combination sensing can beneficial when, for example, the flow sensor fails. The pressure sensor may still be available to detect high drug delivery rates, and this sensor information can be used by the processor or pump controller to shut the pump 102 down to avoid administering an overdose to the patient. In addition, the combination of a flow sensor 180 at the cannula 106 (as shown in FIG. 11) or infusion set 100 (as shown in FIG. 10A) and a pressure sensor at the pump (e.g., a sensor in the pump's drug reservoir) can detect a leak or compromised drug reservoir if pressure is measured in the pump chamber but no flow is measured in the cannula 106 or infusion set 100.

As mentioned above and shown for example in FIG. 11, smart wireless sensors 20, 180 can be employed in medical systems such as, for example, a drug delivery system (e.g., as shown in FIGS. 1, 9, 10B and 11) to measure, detect or sense information about a component of the drug delivery system and/or the drug used therein, and to output (e.g., wireless transmit) data about the measured, detected or sensed property or properties to another device such as a controller or other device internal or external to the a drug delivery system. As described above with reference to US 2008/0129475 and illustrated in FIGS. 1, 9, 10B and 11, the smart sensors 20, 180 can be based on MEMS, SAW and/or RFID technologies whereby information or data or signal from a sensor 20, 180 can be returned to an interrogator provided in the controller or other device that is internal or external to the a drug delivery system and configured for wireless communication with the sensor 20, 180. Further, as described above with reference to US 2008/0129475, the sensors can be configured to receive power wirelessly (e.g., activated upon receiving a transmission of a certain radio frequency (RF) from an interrogator, or inductively as a result of receiving an RF signal which can be in a lower frequency range than an RF communication signal to more efficiently transfer energy in the near field as known in the art).

In accordance with different embodiments, the smart sensor 20, 180 (e.g., illustrated in FIGS. 1, 9, 10A and 11) can be configured to measure at least one parameter related to fluid delivery and/or the drug being delivered such as a physical or chemical parameter or characteristic, and to transfer the measured data to a processor or other control circuitry coupled to the sensor directly (e.g., a processor or control circuit co-located with the sensor in the fluid sensing area or chamber), or remotely (e.g., processor or control circuit located separately from the sensor such as in a related drug-delivery device, device attachment or handheld user interface device with wired or wireless connection to the drug-delivery device).

In accordance with different embodiments, a smart sensor 20 or 180 can be configured to measure two or more different parameters related to fluid delivery and/or the drug being delivered such as physical or chemical parameters or characteristics, and to transfer the measured data to a processor or other control circuitry coupled to the sensor (e.g., directly or remotely as exemplified above). Alternatively, two or more smart sensors 20 or 180 can be deployed to measure different parameters related to fluid delivery and/or the drug being delivered such as physical or chemical parameters or characteristics, and to transfer the measured data to a processor or other control circuitry coupled to the sensor (e.g., directly or remotely as exemplified above).

If analyzing capability is not provided via a processor on micromachined chip(s) in sensor 20, 180, then data can be sent inductively from the sensor 20, 180 to a processor in the pen 2 and/or user interface 22 or pump 102. Flow data can be used to accurately determine completed dose (e.g., a comparison of dosage input with actual amount detected as being delivered based on flow data from sensor 20,180). The flow data can also be used by a processor to determine if a leak or an occlusion has occurred. An indication (e.g., confirmation of complete dose delivery, or warning of incomplete dose, or status indicating leak or occlusion) can be generated on a display (e.g., display 14 on pen 2, display on the user interface 22, or display 104 on a pump 102).

In general, the sensors 20, 180 can be configured to sense any kind of physical or chemical parameter value that may be relevant to the drug being administered or conditions for delivery or dispensing of the fluid such has, but not limited to, pressure, force, temperature, electrical resistance or conductivity, pH, oxygen or other constituent level, flow, and so on. For example, sensor(s) 180 for various pump 102 parameters may be flow, thermal, time of flight, pressure, or other sensors known in the art, and may be fabricated (at least in part) from parylene—a biocompatible, thin-film polymer. Multiple pressure sensors may be used, for example, to detect a difference in pressure and calculate the flow rate based on a known laminar relationship. In the illustrated embodiment of FIG. 11, a flow sensor 180 (e.g., a MEMS sensor) is disposed in the cannula 106 to monitor drug flow to the infusion site, and detect potential obstructions in the flow path, variations in drug-pump pressure, etc.

For example, a sensor 20, 180 can be a microfluidic chip available from Integrated Sensing Systems Inc. that can provide density sensing or Coriolis mass flow sensing. The microfluidic chip sensor employs a chip level silicon tube that can be driven to resonance electrostatically and its motion sensed capacitively using metal electrodes located under the tube and accompanying micromachined electronic circuits connected to the MEMS chip, for example, by wire bonding. Power can be provided to the electronic circuits via an inductive link (e.g., inductive coupling between a receiver coil provided in the electronic circuits associated with the MEMS chip and a transmitter coil and driver provided, for example, in the pen 2, user interface, or pump 102).

A MEMS density or Coriolis mass flow sensor 20 can be provided in the fluid path of a pen 2 or infusion device (e.g., pump 102 and infusion set 100), having a inlet therein that receives sample fluid (e.g., insulin) from a cannula of a drug delivery device (e.g., cannula 24 in the needle adapter 18 for a syringe 2 or cannula 106 connecting an infusion set 100 to a pump 102 or internal cannula with respect to the cartridge provided in the pump and its outlet to the infusion set).

In accordance with another example, a sensor 20, 180 can be a multi-parametric sensor using impedance spectroscopy such as sensors available from S.E.A. Medical Systems, Inc. An impedance spectroscopy sensor can be fabricated using MEMS wherein, for example, variable frequency, low voltage excitation is applied to multiple electrode pairs on a silicon chip (e.g., of dimension 2 mm×2.9 mm or smaller) having, for example, a leadframe, admittance, waveguide and flowmeter as shown in FIG. 11 herein and described with respect to FIG. 13D in U.S. Patent Application Publication No. 2010/0305499 incorporated by reference herein. When the chip is in contact with a particular fluid, an electrical response signature is produced (e.g., see FIG. 19F of US 2010/0305499) that is unique to that fluid due to the fluid's molecular structure or ionic properties.

Such sensing may be particularly useful for determining drug identification (ID), concentration and diluent because of the ability of impedance spectroscopy to distinguish drugs and concentrations. Impedance spectroscopy sensors may also be used to identify expired, degraded or contaminated drugs whose electrical response signatures would be altered from the expected (e.g., previously stored) electrical response signatures of their viable states. In addition to verifying, for example, drug ID and/or concentration, the flowmeter or flow sensor on the chip can detect flow rate and total dose.

The duration of time that such an impedance spectroscopy sensor chip needs to be in contact with a fluid can vary. The chip can be immersed in the fluid being tested, for example, such as using a closed sensor 20 in a pen needle adapter 18 as shown in FIG. 1 or a sensor 20 provided in a cartridge that is attached to a pen 2 (e.g., inserted into the cartridge retaining member 16) as shown in FIG. 2 or placed in a conventional manner in a pump such as the pump 102 shown in FIG. 11. The sensor can, for example, be suspended in the fluid of the cartridge or adhered to an internal surface of the cartridge such as near the cartridge outlet.

The data from the impedance spectroscopy sensor chip can be scanned by a wireless scanner provided in a user interface 22 (e.g., a handheld device 22 that wirelessly communicates with an injection pen 2 having a sensor in its cartridge or in a connected pen needle adapter 18). In the example of a pump, the controller and related electronic components internal to the pump can be configured to receive data from a cartridge having a sensor 20 that is currently inserted into the pump.

The data from the sensor 20 (e.g., a measured electrical response signature from the impedance spectroscopy sensor chip) can be compared with a stored electrical response signature corresponding to the drug that is prescribed to be delivered by the pump (e.g., stored in a memory accessible by a controller in the pump 102 or a wirelessly coupled user interface or portable device 22) to determine if an incorrect drug or a degraded drug has actually been sensed by the sensor 20 in the fluid path of the drug delivery system. The pump 102 and/or the user device 22 can be configured to generate an alert and possible to automatically shut down the pump drive if such an error has been detected.

Illustrative embodiments of the present invention can be implemented, at least in part, in digital electronic circuitry, analog electronic circuitry, or in computer hardware, firmware, software, or in combinations of them. The components of the smart sensors 20, 180 operating in conjunction with a processor or controller associated with the sensor itself, or a drug delivery device 2, 90, 102, or a user interface 22 (e.g., a handheld user device such as a smartphone, laptop, PDM and the like) can be implemented as a computer program product, i.e., a computer program tangibly embodied in an information carrier, e.g., in a machine-readable storage device or in a propagated signal, for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Illustrative embodiments of the present invention have been described with reference to smart sensors 20, 180 operating in conjunction with a processor or controller associated with the sensor itself, or a drug delivery device 2, 90, 102, or a user interface 22 (e.g., a handheld user device such as a smartphone, laptop, PDM and the like), among other components. It is to be understood, however, that the present invention can also be embodied as computer-readable codes on a computer-readable recording medium. The computer-readable recording medium is any data storage device that can store data which can thereafter be read by a computer system. Examples of the computer-readable recording medium include, but are not limited to, read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion.

Also, functional programs, codes, and code segments for accomplishing the present invention can be easily construed as within the scope of the invention by programmers skilled in the art to which the present invention pertains.

Method steps, processes or operations associated with smart sensors 20, 180 operating in conjunction with a processor or controller associated with the sensor itself, or a drug delivery device 2, 90, 102, or a user interface 22 (e.g., a handheld user device such as a smartphone, laptop, PDM and the like), can be performed by one or more programmable processors executing a computer program to perform functions of the invention by operating on input data and generating an output. Method steps can also be performed by, and an apparatus according to illustrative embodiments of the present invention, can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example, semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in special purpose logic circuitry.

The above-presented description and figures are intended by way of example only and are not intended to limit the present invention in any way except as set forth in the following claims. It is particularly noted that persons skilled in the art can readily combine the various technical aspects of the various elements of the various exemplary embodiments that have been described above in numerous other ways, all of which are considered to be within the scope of the invention.

While the invention herein disclosed has been described by means of specific embodiments and applications thereof, numerous modifications and variations can be made thereto by those skilled in the art without departing from the scope of the invention.

The invention claimed is:

1. A system for injecting medicament into a patient via an injection pen having an injection pen housing and used with a replaceable needle assembly for each injection, the system comprising:
   an adapter configured to be detachably coupled between an injection pen housing and a replaceable needle assembly and to deliver the medicament from the injection pen housing to the needle assembly,
   the injection pen housing having a cartridge containing member for receiving a cartridge of medicament and threads on the exterior circumference of a distal end thereof that cooperate with grooves in the interior circumference of the needle assembly to facilitate their coupling and decoupling and replacement of the needle assembly each time the injection pen is used, the adapter comprising
- grooves in the interior circumference of a proximal end thereof that are configured to be the same as the grooves of the needle assembly to cooperate with the threads on the injection pen housing to facilitate coupling and decoupling of the adapter and the injection pen housing,
- a cannula providing a drug throughway from the injection yen housing to a replaceable needle assembly, the cannula having a proximal portion that extends into the injection pen housing when the adapter is coupled to the injection pen housing for fluid path connection with the injection pen housing, and
- threads on the exterior circumference of its distal end that are configured to be the same as the threads on the injection pen housing to cooperate with the grooves in the interior circumference of a replaceable needle assembly to facilitate coupling and decoupling of the adapter and the needle assembly, the cannula having a distal portion that extends into the needle assembly when the adapter is coupled to the needle assembly for fluid path connection with the needle assembly;

a sensor configured as a microchip provided in the adapter to sense the medicament and at least one characteristic about the medicament or its delivery to the patient and generate sensor data; and a device configured to wirelessly communicate with the sensor to obtain its sensor data.

2. A system as claimed in claim 1, wherein the device is a portable user interface.

3. A system as claimed in claim 2, wherein the portable user interface is a mobile phone configured to operate in accordance with an application to interface with the adapter, process the sensor data, set alerts relating to the medicament or its delivery, and generate graph and index information relating to medicament use and degradation for display.

4. A system as claimed in claim 1, wherein the device is configured to obtain wireless transfer of the sensor data and to provide wireless power to the sensor.

5. A system as claimed in claim 1, wherein the device employs one of radio frequency identification (RFID) and surface acoustic wave (SAW) technology for providing wireless power to the sensor.

6. A system as claimed in claim 1, wherein the sensor detects at least one of drug identification and flow rate.

7. A system as claimed in claim 1, wherein the sensor detects dose amount.

8. A system as claimed in claim 1, wherein sensor data is used to estimate insulin on board and confirm quality of dose.

* * * * *